United States Patent [19]

Mossman

[11] Patent Number: 5,138,025

[45] Date of Patent: Aug. 11, 1992

[54] STABILIZED NAPHTHALENEDICARBOXYLIC ACID DIESTERS

[75] Inventor: Allen B. Mossman, Wheaton, Ill.

[73] Assignee: Amoco Corporation, Chicago, Ill.

[21] Appl. No.: 575,068

[22] Filed: Aug. 30, 1990

[51] Int. Cl.$^5$ .............................................. C08J 3/00
[52] U.S. Cl. .................................. 528/298; 528/487; 528/496; 560/3; 560/77; 560/78; 560/98; 560/99; 560/100
[58] Field of Search ...................... 528/298, 487, 496; 560/3, 77, 78, 98, 99, 100

[56] References Cited

U.S. PATENT DOCUMENTS

| | | | |
|---|---|---|---|
| 3,445,504 | 5/1969 | Melhaso | 560/3 |
| 3,461,153 | 8/1969 | Tholstrup et al. | 560/3 |
| 3,505,390 | 4/1970 | Hoffmann | 560/3 |
| 3,742,027 | 6/1973 | Mori et al. | 560/3 |
| 4,048,021 | 9/1977 | Takamoto et al. | 203/91 |
| 4,886,901 | 12/1989 | Holzhauer et al. | 560/77 |

*Primary Examiner*—Samuel A. Acquah
*Attorney, Agent, or Firm*—Thomas E. Nemo; William H. Magidson; Frank J. Sroka

[57] ABSTRACT

A method for stabilizing molten diesters of naphthalenedicarboxylic acids and stabilized naphthalenedicarboxylic acid diester compositions are disclosed.

29 Claims, No Drawings

STABILIZED NAPHTHALENEDICARBOXYLIC ACID DIESTERS

FIELD OF THE INVENTION

This invention relates generally to a method for stabilizing esters of naphthalenedicarboxylic acids. More particularly, this invention relates to a method for stabilizing molten diesters of naphthalenedicarboxylic acids thereby preventing or substantially reducing undesirable degradation of the esters that otherwise occurs during high temperature storage. This invention also relates to novel compositions comprising esters of naphthalenedicarboxylic acids and effective stabilizing compounds.

BACKGROUND OF THE INVENTION

Naphthalenedicarboxylic acids and the diesters of naphthalenedicarboxylic acids are useful chemical intermediates. Naphthalenedicarboxylic acids and diesters of naphthalenedicarboxylic acids, for example, are monomers that can be used to prepare high performance polymeric materials such as polyesters. These naphthalenedicarboxylic acids include 1,2-, 1,3-, 1,4-, 1,5-, 1,6-, 1,7-, 1,8-, 2,3-, 2,6- and 2,7-naphthalenedicarboxylic acid.

2,6-Naphthalenedicarboxylic acid (2,6-NDA) and diesters of 2,6-naphthalenedicarboxylic acid, particularly dimethyl-2,6-naphthalenedicarboxylate (DM-2,6-NDC), can be used to prepare poly(ethylene-2,6-naphthalate) (PEN) by the reaction of 2,6-NDA or a diester of 2,6-NDA with ethylene glycol. Fibers and films made from PEN polyester have improved strength and thermal properties relative to other polyester materials. In addition, films made from PEN demonstrate superior resistance to gas diffusion and particularly to the diffusion of carbon dioxide, oxygen and water vapor. Because of its exceptional properties, PEN is especially useful in applications such as food and beverage containers (particularly in so-called "hot fill" food and beverage containers), tire cord and magnetic recording tape.

Although PEN can be prepared from both 2,6-NDA and DM-2,6-NDC, in some instances it is advantageous to prepare PEN from DM-2,6-NDC. For example, a polyester manufacturer may only have equipment available for storing liquid monomer feed materials and/or for adding liquid feed materials to a polymerization reactor. DM-2,6-NDC would be suitable for this operation whereas the acid, 2,6-NDA, would not. This is because pure DM-2,6-NDC has a melting point of approximately 190° C. and, consequently, can be heated to above its melting point and maintained there in the liquid or molten form. In contrast, 2,6-NDA is a solid that undergoes decomposition at temperatures greater than 300° C. and, therefore, cannot be utilized as a liquid. Additionally, some polyester manufacturers may only have polymerization processes for preparing polyester materials from ester monomers. These manufacturers would necessarily require DM-2,6-NDC, the diester, rather than 2,6-NDA.

Monomer purity is an additional factor that must be considered when deciding whether to manufacture polyesters from diester monomers or diacid monomers. While 2,6-NDA, for example, may be readily obtained by the oxidation of a suitable feedstock such as 2,6-dimethy-, 2,6-diisopropyl- or 2-acetyl-6-methylnaphthalene by one or more oxidation processes, the 2,6-naphthalenedicarboxylic acid obtained therefrom is generally of insufficient purity to be used directly for preparing PEN. Furthermore, 2,6-NDA is extremely difficult to purify. As mentioned above, it does not melt and cannot, therefore, be purified by distillation. It is also essentially insoluble in most common solvents making purification by standard recrystallization processes unsuitable. In contrast, DM-2,6-NDC is a liquid at high temperatures and can be distilled to achieve purity levels required for manufacturing high quality PEN polyester.

Although solid at normal temperatures and pressures it is sometimes preferable to transport and store DM-2,6-NDC as well as the other naphthalenedicarboxylic acid diesters in a molten state. Liquids are easily transferred between storage containers and, as mentioned above, many polyester manufacturers add monomer feeds to polymerization reactors as liquids and consequently prefer to have the monomers supplied as liquids.

While maintaining naphthalenedicarboxylic acid diesters, and particularly DM-2,6-NDC, in the molten state is at times convenient for shipping and for use during the manufacture of PEN or other polymers, the molten diesters degrade at the temperatures used during storage. Although the exact mechanism for the degradation is not known, factors such as the reaction of the hot diester with the oxygen in air, thermal chemical reactions and reaction with ambient moisture, cause a reduction in the quality of the diesters maintained in the molten state. Degradation is undoubtedly accelerated at the high temperatures used for maintaining these diesters and particularly DM-2,6-NDC in the molten state. Additionally, most industrial storage and shipping vessels are constructed of steel. The exposed steel surface in these containers may also promote the degradation of the naphthalenedicarboxylic acid diesters.

The degradation of molten diesters of naphthalenedicarboxylic acids that occurs during high temperature storage results in the discoloration of the ester, an increase in the concentration of acidic materials and in the formation of various impurities. This degradation, particularly the increase in color and the increase in the concentration of impurities that affect the subsequent polymerization step, severely reduces the commercial usefulness of the naphthalenedicarboxylic acid diesters.

One possible method for eliminating or reducing the degradation caused by maintaining the diesters at elevated temperatures is to use molten diesters having one or more stabilizer compounds contained therein. Many stabilizers, for example, anti-oxidants, are commercially available and are used in a variety of applications. These stabilizer compounds include diarylamines such as diphenylamine and di-octyl-diphenylamine, diaryldiamines such as N,N'-diphenyl-p-phenylenediamine and N,N'-di-betanaphthyl-p-phenylenediamine; phenolics such as 2,6-di-t-butylphenol, catechol and pyrogallol; sulfur containing compounds such as dilauryl thiodipropionate; phosphorus-containing compounds such as phosphines, phosphates and phosphites; metal salts of sulfur and phosphorus compounds such as zinc dithiophosphates, as well as a variety of other materials. In particular, certain liquid monomer materials have been stabilized in order to prevent degradation during storage. For example, styrene, a widely used monomer for preparing polystyrene, is stabilized with 4-t-butylcatechol. Molten maleic anhydride may be stabilized with 4,4'-di(hydroxyphenyl) alkanes or with 4-alkylphenols as is disclosed in U.S. Pat. No. 4,062,874 to Sciaraffa and Cermak or, alternatively, with trialkyl trithiophosphites as is taught in U.S. Pat. No. 3,998,854 to Samans and Spatz. Molten dimethylterephthalate may be stabilized with a variety of stabilizer compounds such as a mixture of hindered phenols and dialkyl phosphites as disclosed in U.S. Pat. No. 3,445,504 to Mehalso; ethylene glycol as disclosed in 3,485,867 to Jackson; low molecular weight monohydric saturated alcohols as is disclosed in U.S. Pat. No. 3,505,390 to Hoffmann; catechol, pyrogallol, quinone, hydroquinone, t-butyl catechol, butylated hydroxytoluene, phenol, toluhydroquinone, triphenylphosphite, Primene JMT (t-($C_{18-22}$)-alkyl amines) and Primene 81-R (t-($C_{12-14}$)-alkyl amines) as is disclosed in U.S. Pat. No. 3,659,007 to Giambra; bis-(beta-hydroxyethyl) terephthalate as is disclosed in U.S. Pat. No. 3,742,026 to Mori et al., alkali metal salts or alkoxides plus phosphites as is disclosed in U.S. Pat. No. 4,058,663 to Black and U.S. Pat. No. 3,461,153 to Tholstrup and Rush. None of these disclosures, however, teaches the stabilization of the diesters of naphthalenedicarboxylic acids and, in particular, the stabilization of dimethyl-2,6-naphthalenedicarboxylate.

It would be desirable to have a composition comprising a diester of a naphthalenedicarboxylic acid that does not undergo excessive degradation when stored or used at elevated temperatures. It would also be desirable to have a method for stabilizing liquid esters of naphthalenedicarboxylic acids, and particularly molten dimethyl-2,6-naphthalenedicarboxylate, during shipment or storage at high temperatures. The present invention provides such compositions and methods.

SUMMARY OF THE INVENTION

Provided is a stabilized composition comprising a diester of a naphthalenedicarboxylic acid and a stabilizing effective amount of a stabilizer compound selected from the group consisting of low molecular weight monohydric alcohols and organic phosphites.

Also provided is a method for stabilizing a diester of a naphthalenedicarboxylic acid while maintained in the liquid form and at an elevated temperature comprising treating said diester of a naphthalenedicarboxylic acid with a stabilizing effective amount of a stabilizer compound selected from the group consisting of low molecular weight monohydric alcohols and organic phosphites.

DETAILED DESCRIPTION OF THE PREFERRED EMBODIMENTS

It has been found that the diesters of naphthalenedicarboxylic acids can be stabilized against degradation caused by maintaining these diesters at elevated temperatures. The stabilization is achieved by treating these diesters with organic phosphite compounds or low molecular weight monohydric alcohols.

For the purpose of this invention the term "stabilizing" means preventing or reducing the tendency of the diesters of naphthalenedicarboxylic acids to degrade while being maintained at elevated temperatures and in the liquid state. "Elevated temperatures" as used herein means those temperatures above the melting point of the respective naphthalenedicarboxylic acid diester. For example, the melting point of pure dimethyl-2,6-naphthalenedicarboxylic acid is approximately 190° C. Therefore, an elevated temperature with respect to dimethyl-2,6-naphthalenedicarboxylate is a temperature in excess of approximately 190° C. More preferably, "elevated temperature" is a temperature from about the melting temperature of the diester to about 50° C., and most preferably about 20° C., above the melting temperature. The melting temperature of the diester of naphthalenedicarboxylic acid will, of course, depend on the purity of the diesters. By "degradation" it is meant, a decrease in the purity of the diester material. Most suitably, this degradation can be quantified by measuring the color of the degraded diester. Pure diester materials of this invention are colorless, or nearly colorless, in the molten state. Consequently, any development of color or increase in color is an indication of an increase in the level of one or more impurities. Measurement of the levels of specific acidic components is another method for determining the degradation of the diester caused by maintaining the diesters of naphthalenedicarboxylic acid at elevated temperatures. For example, increased levels of 2,6-naphthalenedicarboxylic acid or momo-methyl-2,6-naphthalenedicarboxylate is an indication of the degree of degradation of pure dimethyl-2,6-naphthalenedicarboxylate.

The diesters used in the compositions and method of this invention are the diesters of the naphthalenedicarboxylic acids which include 1,2-, 1,3-, 1,4-, 1,5-, 1,6-, 1,7-, 1,8-, 2,3-, 2,6- and 2,7-naphthalenedicarboxylic acid and preferably wherein the radicals bonded to the oxygen atoms of the diester molecule contain 1–6 carbon atoms, and which may be the same or different, and which may be branched, linear or cyclic, e.g., methyl, ethyl, propyl, isopropyl, n-butyl, iso-butyl, tert-butyl, n-pentyl, all branched pentyl radicals, cyclopentyl, n-hexyl, all branched hexyl radicals and cyclohexyl. Diesters of 2,6-naphthalenedicarboxylic acid are the preferred esters used in the method and compositions of this invention. These aforementioned diesters are suitabley prepared by esterifying the respective naphthalenedicarboxylic acid with a monohydric alcohol, although they may also be prepared by other methods. Preferably, these alcohols contain 1 to 6 carbon atoms and may be linear, branched or cyclic, e.g., methanol, ethanol, propanol, isopropanol, n-butanol, iso-butanol, sec-butanol, n-pentanol, all isomeric branched pentanols, n-hexanol, all branched hexanols and cyclohexanol. Alcohols containing 3–6 carbon atoms may be a secondary or tertiary alcohol as well as a primary alcohol. Mixtures of these alcohols are also suitable.

Methanol, however, is the preferred alcohol for esterifying the naphthalenedicarboxylic acids of this invention. The dimethyl esters of the naphthalenedicarboxylic acids are highly preferred diester materials. Dimethyl-2,6-naphthalenedicarboxylate is the most preferred diester for the method and compositions of this invention.

Methods for preparing esters of aromatic carboxylic acids such as naphthalenedicarboxylic acids are well known in the art. For example, an aromatic dicarboxylic acid, such as one of the aforementioned naphthalenedicarboxylic acids, can be converted to its dimethyl ester by esterification with methanol in the presence of an esterification catalyst at an elevated temperature and/or elevated pressure. Suitably, the esterification catalyst is sulfuric acid, p-toluene sulfonic acid, methane sulfonic acid, a titanium alkoxide, zinc oxide, molybdenum trioxide or organic tin compound. For example, to prepare the dimethyl ester of a naphthalenedicarboxylic acid the crude naphthalenedicarboxylic acid, methanol and an 80–85 weight percent solution of sulfuric acid in water are mixed in a weight ratio of 1:8:0.1 and heated to 120° C. with agitation and held at that temperature for about 6 hours. The mixture is then cooled to a temperature between 20° C. and 65° C. to crystallize the dimethylnaphthalenedicarboxylate, and the resulting crude dimethylnaphthalenedicarboxylate is separated from the mother liquor, for example, by filtration or centrifugation. A methanol wash may be used to remove sulfuric acid. The resulting dimethylnaphthalenedicarboxylate can be, and preferably is, purified further by either a recrystallization procedure from a solvent such as methanol or by fractional distillation. Methods for preparing and purifying dimethylnaphthalenedicarboxylates are disclosed in U.S. Pat. No. 4,886,901 to Holzhauer et al., the specification of which is specifically incorporated herein by reference. A method for purifying dimethyl-2,6-naphthalenedicarboxylate by vacuum distillation is disclosed in U.S. Pat. No. 4,048,021 to Takamoto et al. The diesters of the naphthalenedicarboxylic acids used in the composition and method of this invention are preferably substantially pure. Suitably, the diesters used in the method and compositions of this invention have a purity of at least 98% (wt. %), more preferably a purity greater than 99% (wt. %), and most preferably a purity of greater than 99.5% (wt. %). Preferably, the naphthalenedicarboxylic acid diesters of this invention have been purified by distillation and/or crystallization or some other means to eliminate or substantially reduce impurities such as trimethyltrimellitates, naphthalene ring-brominated compounds and methylformyl naphthoic acids.

Preferably, the naphthalenedicarboxylic acid diesters of this invention are prepared from naphthalenedicarboxylic acids that have been prepared by the oxidation of the corresponding dialkylnaphthalene compound wherein the alkyl groups contain 1–3 carbon atoms. Preferably the alkyl groups are methyl groups.

Dimethyl substituted naphthalene compounds may be isolated from, for example, refining or coal-derived streams. More directly, these dimethyl substituted compounds can be prepared by methods known in the art. For example, U.S. Pat. No. 4,950,825, to Sikkenga et al., the specification of which is hereby incorporated by reference, discloses a preferred method for preparing the preferred dimethylnaphthalenes. A method for preparing 2,6-diethylnaphthalene, which is also a preferred feed for oxidation to 2,6-naphthalenedicarboxylic acid, is disclosed in U.S. Pat. No. 4,873,386 to Hagen et al.

The preferred method for oxidizing the dialkylnaphthalene compounds, and most preferably 2,6-dimethylnaphthalene, to the corresponding naphthalenedicarboxylic acid comprises a liquid phase oxidation using a source of molecular oxygen, a metal catalyst and a suitable solvent.

Suitable solvents for use in the aforementioned liquid phase oxidation of dialkylnaphthalenes include benzoic, any aliphatic $C_2$–$C_6$ monocarboxylic acid such as acetic acid, propionic acid, n-butyric acid, isobutyric acid, n-valeric acid, trimethylacetic acid, caproic acid, water, and mixtures thereof. Preferably, the solvent is a mixture of acetic acid and water, which more preferably contains from 1 to 20 weight percent of water, as introduced into the oxidation reactor. Heat generated in the highly exothermic liquid-phase oxidation is dissipated at least partially by vaporization of solvent in the oxidation reactor as a vapor, which is then condensed and recycled to the reactor.

In addition, some solvent is withdrawn from the oxidation reactor as a liquid in the product stream. After separation of the crude naphthalenedicarboxylic acid product from the product stream, at least a portion of the mother liquor (solvent) in the resulting product stream is generally recycled to the oxidation reactor.

The source of molecular oxygen employed in the aforementioned liquid-phase oxidation of dialkylnaphthalenes can vary in molecular oxygen content from that of air to oxygen gas. Air is the preferred source of molecular oxygen. In order to avoid the formation of explosive mixtures, the oxygen-containing gas fed to the reactor preferably should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the aforementioned liquid-phase oxidation of dialkylnaphthalenes comprises a bromine-containing component and at least one of a cobalt- and manganese-containing component, and can additionally comprise accelerators known in the art. Preferably, the catalyst comprises cobalt-, manganese-, and bromine-containing components. Preferably, the weight ratio of cobalt (calculated as elemental cobalt) in the cobalt component of the catalyst-to-the dialkylnaphthalene in the liquid-phase oxidation is in the range of from about 0.1 to about 20 milligram atoms (mga) per gram mole of dialkylnaphthalene. Preferably, the weight ratio of manganese (calculated as elemental manganese) in the manganese component of the catalyst-to-cobalt (calculated as elemental cobalt) in the cobalt component of the catalyst in the liquid-phase oxidation is in the range of from about 0.1 to about 20 mga per mga of cobalt. Preferably, the weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 3.0 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 3.0:1.0 bromine-to-total cobalt and manganese milligram atom ratio is provided by a suitable source of bromine. Such bromine sources include elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.1:1.0 to 3.0:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is preferably that pressure which will maintain a substantial liquid phase of the dialkylnaphthalene and at least 70 percent of the solvent. The dialkylnaphthalene and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0.1 kg/cm$^2$ to about 35 kg/cm$^2$, and typically are in the range of from about 10 kg/cm$^2$ to about 30 kg/cm$^2$. The temperature range within the oxidation reactor is generally about 120° C., preferably from about 150° C., to about 240° C., preferably to about 230° C. The solvent residence time in the oxidation reactor is generally about 20 to about 150 minutes and preferably from about 30 to about 120 minutes.

The aforementioned liquid phase oxidation of the dialkylnaphthalenes can be performed either in the batch, continuous, or semi-continuous mode. In the batch mode, the dialkylnaphthalene, solvent and the catalyst components are initially introduced batchwise into the reactor, and the temperature and pressure of the reactor contents are then raised to the desired levels therefor for the commencement of the oxidation reaction. Air is introduced continuously into the reactor. After commencement of the oxidation reaction—for example, after all of the dialkylnaphthalene has been completely introduced into the reactor—the temperature of the reactor contents is raised.

In the continuous mode, each of the dialkylnaphthalene, air, solvent, and catalyst are continuously introduced into the reactor, and a product stream comprising naphthalenedicarboxylic acid and catalyst components dissolved in the solvent is withdrawn from the reactor. In a semicontinuous mode, the solvent and catalyst are initially introduced into the reactor and then the dialkylnaphthalene and air are continuously introduced into the reactor.

Thereafter, the product stream in the continuous mode or the reactor contents in the batch or semicontinuous mode are cooled to a temperature in the range of from about 80° C. to about 105° C. in at least one step and in at least one crystallizer such that essentially all of the naphthalenedicarboxylic acid crystallizes in the solvent. Following crystallization, the resulting slurry of naphthalenedicarboxylic acid in the mother liquor is separated, typically by centrifugation, at a temperature in the range of from about 80° C. to about 105° C. Generally the separation is performed at essentially the same temperature as the final crystallization temperature.

For the preferred embodiements of this invention the diesters of the naphthalenedicarboxylic acids disclosed herein are prepared by the oxidation of a dialkyl substituted naphthalene compound to the corresponding naphthalenedicarboxylic acid, followed by the esterification of the naphthalenedicarboxylic acid with a low molecular weight alcohol. However, other sources of the naphthalenedicarboxylic acids and diesters of naphthalenedicarboxylic acids are also suitable for the compositions and method disclosed herein, such as the oxidation of a methylacylnaphthalene, e.g. the oxidation of 2-acetyl-6-methylnaphthalene to 2,6-naphthalenedicarboxylic acid, followed by esterification of the diacid to a diester, or the diesters made from naphthalenedicarboxylic acids made by the so-called Henkel process.

The stabilizer compounds of this invention that are effective for preventing or reducing the degradation of diesters of naphthalenedicarboxylic acids maintained in a liquid form at an elevated temperature comprise compounds selected from organic phosphites and low molecular weight alcohols.

For the purpose of this invention, organic phosphites are those phosphites having pendant organic groups and preferably include those organo-phosphorus compounds having structures (I) and (II) as shown below:

(I)

(II)

wherein R is a hydrocarbyl or substituted hydrocarbyl group and which may be the same or different within each chemical structure shown. Preferably R is a hydrocarbyl group of from 1 to 25 carbon atoms and may be an alkyl group that is branched, cyclic or straight chain such as, for example, methyl, ethyl, propyl, isopropyl, butyl, amyl, cyclohexyl, octyl, 2-ethylhexyl, lauryl, stearyl, tetracosyl etc.; an aryl group of from 6 to 24 carbon such as, for example, phenyl, tolyl, naphthalene; an aralkyl group containing 7 to 25 carbon atoms such as, for example, benzyl, octyl and nonyl phenyl, etc.; or an alkenyl group containing 2 to 25 carbon atoms such as, for example, oleyl, hexenyl, propenyl etc. Additionally, the hydrocarbyl group may contain one or more substituents that do not interfere with the performance of the organic phosphite stabilizer compound. Mixtures of organic phosphites are also suitable as stabilizers.

Structure (I) above hereinafter represents organic tri-phosphites, and structure (II) above represents organic di-phosphites. In the method and compositions of this invention, the preferred organic phosphite stabilizer compounds are dimethyl and diphenyl phosphite and trimethyl and triphenyl phosphite. Other preferred phosphites are the di- and tri-phosphites wherein R in structures I and II is ethyl, propyl, isopopyl, amyl, 2-ethyl-hexyl, isoctyl, isononyl, cyclohexyl, tolyl, octylphenyl, nonylphenyl or mixtures thereof.

The organic phosphites of this invention may be purchased from commercial sources such as the Aldrich Chemical Company, Milwaukee, Wisconsin and/or may be prepared by the reaction of an alcohol or phenol or mixture thereof with phosphorus trichloride according to procedures well known in the art. For example, by reacting phosphorus trichloride with an alcohol or phenol in the presence of a base such as pyridine, the organic triphosphites of this invention are formed. In the absence of the base, the organic di-phosphites of this invention are formed. J. R. Van Wazer, "Phosphorus and Its Compounds," Vol. II, pp. 1267–1271, Interscience Publishers, 1961, discloses methods known in the art for preparing organic phosphites.

In the method and compositions of this invention, the amount of organic phosphite used as a stabilizer compound in the naphthalenedicarboxylic acid diester is an amount sufficient to reduce or eliminate the degradation of the diester when the diester is maintained in the molten state and at an elevated temperature. Suitably, the amount of organic phosphite present is about 0.01 to about 10,000 parts per million by weight (ppm) relative to the diester, preferably about 0.01 to about 500 ppm and most preferably about 1 to about 100 ppm. In some instances, however, it is preferably to limit the amount of organic phosphite to 50 ppm and less than about 50 ppm, i.e., an amount in the range of about 0.01 ppm to about 50 ppm. This is the case where the amount of phosphite added, while stabilizing the color, actually causes an increase in acidic impurities. Consequently, for some diesters used with certain organic phosphites wherein it is desirable to limit the increase in formation of acid impurities, it may be necessary to limit the amount of organic phosphite to about 50 ppm and below.

The time period during which the stabilized diester compositions of this invention are held in the molten state may vary depending on the given application. For example, this time period may vary up to about 21 days, preferably the time period is from about 0.5 hour to about 10 days.

The low molecular weight monohydric alcohol stabilizer compounds of the method and compositions of this invention are preferably those alcohols having 1 to 4 carbon atoms as, for example, methanol, ethanol, propanol, isopropanol, n-butanol, isobutanol, secondary butanol and t-butyl alcohol. The most preferred alcohol is methanol. Mixtures of these alcohols are also suitable. The amount of low molecular weight alcohol used as a stabilizer for the naphthalenedicarboxylic acid diesters disclosed herein is an amount sufficient to reduce or eliminate the degradation of the naphthalenedicarboxylic acid diester when the diester is maintained in the molten state at an elevated temperature. Preferably, the amount of low molecular weight alcohol relative to the diester is about 1 to about 20,000 ppm, more preferably about 50 to about 10,000 ppm and most preferably 250 to about 8,000 ppm. The low molecular weight alcohols, and particularly methanol, are especially suitable stabilizer compounds due to their relatively low vapor pressures. For example, when a diester of a naphthalenedicarboxylic acid is used for the preparation of a polyester material, the low molecular weight alcohol stabilizers of this invention are eliminated from the polymerization mixture during the heating process. Methanol is particularly preferred for stabilizing the dimethylnaphthalenedicarboxylates because methanol is also eliminated from these diesters when they are heated to make polyesters.

The method of adding the stabilizer compounds of this invention to the naphthalenedicarboxylic acid diesters is not a critical aspect of this invention. All means and methods for adding the stabilizer compounds are suitable. For example, the stabilizers may be added immediately after the manufacture of the naphthalenedicarboxylic acid diester while the diester is still liquid. Alternatively, the stabilizer compound may be added to solid diesters and would, therefore, be present while diester is being heated for melting. The stabilizer may also be added all at once, in stages, or continuously throughout the storage period. Additionally, it has been found that the stabilizers of this invention are effective when the atmosphere above the stored molten diester is an inert atmosphere, such as a nitrogen atmosphere, or when the atmosphere is air or contains air. Furthermore, the molten diester may contain moisture, and the atmosphere above the diester may also contain moisture. The method and compositions of this invention are also suitable where the vessel used for storing or transporting the molten diester is made of steel wherein the diester is exposed to a steel surface. Consequently, by using the compositions and method of this invention it is not required to take extraordinary precautions regarding the material of construction of the vessel used for storing or transporting the molten esters, i.e., they need not be made of inert materials such as glass. Although it is not necessary to preclude moisture and air from the storage vessel, it is nevertheless preferable to do so.

An additional aspect of this invention is the method of preparing polyesters, preferably poly (ethylene-2,6-naphthalate) (PEN), using diesters of naphthalenedicarboxylic acids, preferably dimethyl-2,6-naphthalenedicarboxylate, and a diol, preferably ethylene glycol, wherein the diester feed material to the polymerization process contains a stabilizer of this invention. These diols include any diols containing 1 to 8 carbon atoms including, for example, ethylene glycol, propylene glycol, butane diol, 1,2-, 1,3- and 1,4-cyclohexane diol and 1,2-, 1,3- and 1,4-cyclohexanedimethanol. In a typical process for preparing PEN, dimethyl-2,6-naphthalenedicarboxylate is mixed with excess ethylene glycol in the presence or absence of a transesterification catalyst such as manganese, cobalt, calcium or mixtures thereof in a suitable reaction vessel. This mixture is heated to prepare a so-called pre-polymer. This pre-polymer comprises oligomeric materials and materials such as bis-2-hydroxyethyl-naphthalate. In a second step, the pre-polymer mixture is heated, typically under vacuum, in the presence of a catalyst such as antimony oxide to remove excess ethylene glycol and form the high molecular weight PEN polymer. In a preferred process of this invention, the dimethyl-2,6-naphthalenedicarboxylate feed to a polymerization process for making PEN contains a stabilizing effective amount of a stabilizer selected from the group consisting of organic phosphites and low molecular weight monohydric alcohols. Preferably the stabilizers are selected from triphenyl phosphite, diphenyl phosphite, trimethyl phosphite, dimethyl phosphite and methanol.

The following examples are presented to illustrate the present invention without intending to limit the scope thereof.

YIE MEASUREMENTS

YIE is a measure of the "yellowness" of a chloroform solution of the naphthalenedicarboxylic acid diesters disclosed herein. As stated above, color change may be used to monitor the degradation of the diesters during storage at elevated temperatures. Any method, for example, even a visual method, can be used to monitor color change. Use of an instrument to quantify color levels, however, provides for more consistent and more easily comparable data.

The YIE values for the samples of dimethyl-2,6-naphthalenedicarboxylate disclosed in the Examples herein were measured on a Gardner XL-835 tri-stimulus colorimeter using quartz sample cells. Measurements were taken on 0.75 gram samples of dimethyl-2,6-naphthalenedicarboxylate dissolved in 25 ml of chloroform. Before YIE measurements were taken, the samples were filtered to remove any particulates. (See ASTM method E-313, "Indexes of Whiteness and Yellowness of Near-White, Opaque Materials"). As disclosed herein, corrected YIE (CYIE) is the YIE measured for the sample of interest minus the YIE measured for a solvent blank.

EXAMPLE 1

Table I presents the results of the evaluation of 34 materials as stabilizers for dimethyl-2,6-naphthalenedicarboxylate. The evaluations were conducted at 205° C. for 168 hours. Each 20 gram test sample contained a piece of 316-1 steel, 1¾ inches long by ¼ inch round, to simulate the effect of a steel storage container. Stabilizers were evaluated at treat levels of approximately 100, 1,000, 5,000 and, for methanol and ethylene glycol, at 10,000 parts per million by weight. Evaluations were conducted in air using dimethyl-2,6-naphthalenedicarboxylate that was not previously dried. Evaluations were also conducted in a nitrogen atmosphere using samples of dimethyl-2,6-naphthalenedicarboxylate that were first dried in a vacuum oven at 80° C. for 16 hours before being treated with the stabilizer. Balloons filled with nitrogen or air and fixed to the tops of the glass containers used to hold the dimethyl-2,6-naphthalenedicarboxylate ester samples supplied the nitrogen or air atmospheres. The degree of degradation of the samples was measured by YIE color measurement. Table I reports corrected YIE values (CYIE). Each of the CYIE values reported in Table I corresponds to one test sample, except for the CYIE values reported for the samples run with no stabilizer. These are averages of 25 runs. The fresh dimethyl-2,6-naphthalenedicarboxylate used in the following examples had a CYIE of 0.05 and contained less than 4 ppm 2,6-naphthalenedicarboxylic acid, and less than 2 ppm mono-methyl-2,6-naphthalenedicarboxylate.

TABLE I

Stabilization of Dimethyl-2,6-Naphthalenedicarboxylate[a]

| Stabilizer | Corrected YIE[b] | | | | | | | |
|---|---|---|---|---|---|---|---|---|
| | 100 ppm[c] | | 1000 ppm[c] | | 5000 ppm[c] | | 10,000 ppm[c] | |
| | Air[d] | N2[e] | Air | N2 | Air | N2 | Air | N2 |
| Triphenyl phosphite | 3.98 | 2.91 | 9.5 | 4.00 | 29.74 | 10.30 | | |
| Diphenyl phosphite | 4.28 | 2.77 | 8.63 | 4.12 | 22.73 | 7.39 | | |
| Dimethyl phosphite | 4.34 | 2.43 | 5.26 | 2.59 | 6.66 | 2.08 | | |
| TBHMPS[f] | 8.03 | 6.95 | 29.57 | 21.96 | 46.57 | 36.92 | | |
| Trimethyl phosphite | 8.41 | 3.27 | 6.96 | 2.21 | 11.83 | 4.55 | | |
| Diphenyl phosphite + TBHMPS[f] | 9.97 | 4.18 | — | — | — | — | | |
| Pyrogallol | 10.98 | 3.88 | 9.80 | 8.36 | 7.09 | 5.20 | | |
| Diphenyl carbonate | 14.12 | 12.62 | 9.16 | 7.47 | 13.00 | 9.66 | | |
| Diphenyl Methane | 14.25 | 9.81 | 11.77 | 6.54 | 23.71 | 13.59 | | |
| p-quinone | 15.01 | 18.56 | 23.27 | 8.76 | 12.2 | 8.54 | | |
| Pre-polymer A[g] | 15.75 | 9.35 | 17.62 | 6.89 | 12.37 | 7.06 | | |
| Triphenyl methane | 16.17 | 7.47 | 22.29 | 14.93 | 32.51 | 26.89 | | |
| Ethylene diacetate | 16.2 | 8.73 | 14.18 | 7.97 | 17.35 | 12.67 | | |
| Ethyl alcohol | 16.24 | 14.73 | 21.60 | 9.13 | 13.64 | 5.72 | | |
| Mono-methyl-2,6-NDC, Na salt | 17.53 | 10.86 | 24.91 | 11.02 | 23.17 | 14.09 | | |
| Methanol | 18.37 | 13.23 | 19.37 | 11.75 | 11.67 | 4.93 | 11.25 | 11.20 |
| Phenol | 18.51 | 10.65 | 31.86 | 20.54 | 45.19 | 34.35 | | |
| 2,5-di-t-butyl hydroquinone | 19.16 | 12.74 | 38.46 | 22.70 | 52.83 | 26.38 | | |
| 3,5-di-t-butyl catechol | 19.28 | 17.38 | 42.35 | 34.22 | 52.53 | 26.72 | | |
| Citric acid | 19.5 | 10.99 | 25.27 | 18.67 | 46.06 | 36.28 | | |
| Propylene glycol | 19.65 | 10.65 | 21.00 | 18.52 | 37.56 | 29.33 | | |
| Hydroquinone | 20.09 | 11.76 | 45.08 | 41.10 | 57.09 | 36.26 | | |
| Catechol | 20.96 | 18.16 | 30.95 | 23.62 | 40.03 | 22.89 | | |
| Ethylene glycol | 22.06 | 14.21 | 17.91 | 10.70 | 15.11 | 8.74 | 22.51 | 23.96 |
| Pre-polymer B[h] | 22.78 | 15.8 | 17.79 | 13.78 | 20.38 | 14.85 | | |
| Methyl hydroquinone | 24.66 | 15.22 | 44.57 | 19.23 | 18.76 | 8.84 | | |
| 4-t-butyl catechol | 27.05 | 19.4 | 54.17 | 33.83 | 72.79 | 53.72 | | |
| Hydroquinone monomethyl ether | 30.04 | 17.17 | 54.11 | 29.03 | 73.03 | 53.96 | | |
| Potassium hydroxide | 31.81 | 19.69 | 38.29 | 22.26 | 39.76 | 19.83 | | |
| Potassium acetate | 34.45 | 26.01 | 50.89 | 44.02 | 53.51 | 42.42 | | |
| Potassium biphthalate | 45.67 | 23.46 | 59.19 | 42.44 | 59.49 | 53.88 | | |
| Sodium acetate | 46.43 | 40.19 | 58.50 | 45.09 | 53.79 | 28.48 | | |
| Sodium benzoate | 49.49 | 33.93 | 60.05 | 34.64 | 52.69 | 33.55 | | |
| Potassium benzoate | 61.92 | 26.85 | 51.40 | 45.65 | 52.48 | 42.81 | | |
| No stabilizer[i] | 16.77 | 11.48 | 16.77 | 11.48 | 16.77 | 11.48 | 16.77 | 11.48 |

Footnotes for Table I:
[a]Samples held at 205° C. for 168 hours with a piece of 316-1 steel in the sample.
[b]Yellowness of a 0.75 g sample dissolved in 25 ml of chloroform and filtered.
[c]Parts per million by weight (approximate values).
[d]Air atmosphere, DM-2,6-NDC not dried.
[e]Nitrogen atmosphere, DM-2,6-NDC dried for 18 hours at 80° C. in a vacuum oven.
[f]3-t-Butyl-4-hydroxy-5-methyl phenyl sulfide.
[g]See Example 12.
[h]See Example 13.
[i]Values are an average of 25 runs for the samples without a stabilizer added.

The YIE data in Table I demonstrates the superior stabilization provided by triphenyl phosphite, diphenyl phosphite, dimethyl phosphite and trimethyl phosphite. Stabilization was provided by these materials in both nitrogen and air atmospheres. Triphenyl phosphite, diphenyl phosphite and dimethyl phosphite were particularly effective at the 100 ppm level. Many standard stabilizer materials such as the phenolic type stabilizers, i.e. phenol, 2,5-di-t-butyl hydroquinone, 3,5-di-t-butyl catechol and 4-t-butyl catechol were not effective. While pyrogallol provided stabilization at 5000 ppm, dark particulate matter developed in the samples making pyrogallol an unsuitable stabilizer.

Examples 2-11 are detailed evaluations of ten stabilizer materials. As in Example 1, these samples were also evaluated at 205° C. for 168 hours with a piece of 316-1 steel contained in the sample. Air and nitrogen atmospheres on non-dried and dried ester samples, respectively, were also used. For these evaluations ballons were not used to maintain the air and nitrogen atmospheres. For Examples 2-8, the stabilizers were evaluated at treat levels of approximately 5, 12.5, 25, 50, 125, 250 and 500 parts per million by weight relative to dimethyl-2,6-naphthalenedicarboxylate. Higher treat levels were used in Examples 9-11.

The degree of degradation of the dimethyl-2,6-naphthalenedicarboxylate was determined by YIE measurements. Both corrected YIE (CYIE) and reduced YIE (RYIE) values are listed in the attached tables. The reduced YIE (RYIE) values are obtained by dividing the CYIE value obtained from the stabilizer-treated sample by the CYIE value obtained from the sample without stabilizer. The RYIE values provide for a reliable method of comparing the different stabilizers. The RYIE values may be used to quantify the effectiveness of the stabilizers disclosed herein. Preferably, the stabilized diester compositions of this invention should have RYIE values of about 0.5 and below, and more preferably of about 0.3 and below after being maintained in the molten state under a nitrogen atmosphere for about 168 hours. The degree of degradation of the dimethyl-2,6-naphthalenedicarboxylate was also determined by measuring the levels of 2,6-naphthalenedicarboxylic acid (2,6-NDA) and mono-methyl-2,6-naphthaledicarboxylate (MM-2,6-NDC). Liquid chromatography was used to measure the 2,6-NDA and MM-2,6-NDC levels. Liquid chromatography measurements were made using a Waters Nova-Pak, 4 micrometer column. The solvent system was a mixture of water and acetonitrile. The gradient was 5% to 95% acetonitrile.

EXAMPLES 2–5

Tables II through V provide data showing the excellent stabilization of dimethyl-2,6-naphthalenedicarboxylic provided by triphenyl phosphite (Example 2), diphenyl phosphite (Example 3), trimethyl phosphite (Example 4), and dimethyl phosphite (Example 5), respectively. Reduction in color as measured by RYIE and reduction in the levels of acidic impurities was readily achieved by employing low levels of these stabilizer materials. For example, 25 ppm of triphenyl phosphite provides for a RYIE of 0.20 and a greater than 50% reduction in the formation of MM-2,6-NDC in a sample of dimethyl-2,6-naphthalenedicarboxylate heated under a nitrogen atmosphere for 168 hours at 205° C. compared to a sample of dimethyl-2,6-naphthalenedicarboxylate without a stabilizer added.

TABLE II

| | Stabilization of DM-2,6-NDC with Triphenyl Phosphite[a] | | | | | | | |
|---|---|---|---|---|---|---|---|---|
| | Air[b] | | | | Nitrogen[c] | | | |
| Stab. ppm | CYIE[d] | RYIE[e] | ppm[f] NDA | ppm[g] MM NDC | CYIE | RYIE | ppm NDA | ppm MM NDC |
| 0 | 10.96 | 1 | 0 | 1268 | 2.09 | 1 | 8.4 | 716 |
| 5 | 5.15 | 0.47 | 0 | 873 | 1.09 | 0.52 | 15.3 | 365 |
| 12.5 | 4.35 | 0.40 | 4.6 | 540 | 0.68 | 0.33 | 0 | 236 |
| 25 | 4.13 | 0.38 | 0 | 869 | 0.41 | 0.20 | 0 | 420 |
| 50 | 3.66 | 0.33 | 0 | 976 | 0.48 | 0.23 | 6.6 | 565 |
| 125 | 3.30 | 0.30 | 0 | 1812 | 0.34 | 01.6 | 20.9 | 1027 |
| 250 | 3.14 | 0.29 | 4.9 | 1655 | 0.18 | 0.09 | 17.5 | 1042 |
| 500 | 3.21 | 0.29 | 7.5 | 2392 | 0.28 | 0.13 | 7.1 | 1412 |
| 0 | | | | | 2.0 | 1 | 0 | 1075 |
| 5 | | | | | 0.99 | 0.50 | 0 | 523 |
| 12.5 | | | | | 0.65 | 0.33 | 0 | 473 |
| 25 | | | | | 0.32 | 0.16 | 0 | 406 |
| 50 | | | | | 0.47 | 0.24 | 0 | 775. |
| 125 | | | | | 0.19 | 0.10 | 0 | 863 |
| 250 | | | | | 0.20 | 0.10 | 0 | 1316 |
| 500 | | | | | 0.24 | 0.12 | 4 | 1152 |

Footnotes for Table II:
[a]Samples held at 205° C. for 168 hours with a piece of 316-1 steel contained in the sample.
[b]Air atmosphere, sample not dried.
[c]Nitrogen atmosphere, sample previously dried at 80° C. for 16 hours in a vacuum oven.
[d]Corrected YIE after 168 hours at 205° C.
[e]Reduced YIE after 168 hours at 205° C.
[f]Parts per million 2,6-naphthalenedicarboxylic acid after 168 hours at 205° C.
[g]Parts per million mono-methyl-2,6-naphthalenedicarboxylate after 168 hours at 205° C.

TABLE III

| | Stabilization of DM-2,6-NDC with Diphenyl Phosphite[a] | | | | | | | |
|---|---|---|---|---|---|---|---|---|
| | Air | | | | Nitrogen | | | |
| Stab. ppm | CYIE | RYIE | ppm NDA | ppm MM NDC | CYIE | RYIE | ppm NDA | ppm MM NDC |
| 0 | 11.7 | 1 | 0 | 1363 | 0.81 | 1 | 0 | 1176 |
| 5 | 4.37 | 0.37 | 0 | 500 | 0.64 | 0.79 | 6.1 | 405 |
| 12.5 | 4.31 | 0.37 | 0 | 389 | 0.29 | 0.36 | 6.6 | 313 |
| 25 | 4.59 | 0.39 | 0 | 699 | 0.24 | 0.30 | 0 | 406 |
| 50 | 4.1 | 0.35 | 0 | 842 | 0.25 | 0.31 | 5.4 | 595 |
| 125 | 3.43 | 0.29 | 5.9 | 1871 | 0.20 | 0.25 | 4.3 | 1231 |
| 250 | 3.01 | 0.26 | 9.8 | 2054 | 0.23 | 0.28 | 4.4 | 1430 |
| 500 | 3.20 | 0.27 | 14.1 | 2459 | 0.28 | 0.35 | 7.4 | 1662 |

[a]See Table II for explanation of abbreviations.

TABLE IV

| | Stabilization of DM-2,6-NDC with Trimethyl Phosphite[a] | | | | | | | |
|---|---|---|---|---|---|---|---|---|
| | Air | | | | Nitrogen | | | |
| Stab. ppm | CYIE | RYIE | ppm NDA | ppm MM NDC | CYIE | RYIE | ppm NDA | ppm MM NDC |
| 0 | 12.65 | 1 | 5.3 | 1164 | 1.41 | 1.0 | 31.01 | 1718 |
| 5 | 9.89 | 0.78 | 5.0 | 940 | 1.0 | 0.71 | 0 | 1233 |

TABLE IV-continued

Stabilization of DM-2,6-NDC with Trimethyl Phosphite[a]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 12.5 | 5.20 | 0.41 | 10.4 | 532 | 1.08 | 0.77 | 0 | 564 |
| 25 | 3.26 | 0.26 | 9.7 | 490 | 0.83 | 0.59 | 0 | 666 |
| 50 | 4.48 | 0.35 | 7.5 | 495 | 0.50 | 0.35 | 0 | 469 |
| 125 | 4.11 | 0.32 | 0 | 383 | 0.47 | 0.33 | 0 | 551 |
| 250 | 4.87 | 0.38 | 0 | 705 | 0.26 | 0.18 | 0 | 589 |
| 500 | 3.98 | 0.31 | 0 | 866 | 0.23 | 0.16 | 0 | 978 |

[a]See Table II for explanation of abbreviations.

TABLE V

Stabilization of DM-2,6-NDC with Dimethyl Phosphite[a]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 0 | 7.53 | 1 | 4.5 | 1052 | 0.94 | 1 | 7.7 | 1154 |
| 5 | 4.94 | 0.66 | 8.9 | 631 | 0.38 | 0.40 | 0 | 448 |
| 12.5 | 4.32 | 0.57 | 0 | 492 | 0.46 | 0.49 | 0 | 488 |
| 25 | 4.01 | 0.53 | 0 | 654 | 0.39 | 0.41 | 0 | 398 |
| 50 | 4.50 | 0.60 | 0 | 1258 | 0.25 | 0.27 | 5.0 | 702 |
| 125 | 2.83 | 0.38 | 8.5 | 1892 | 0.30 | 0.32 | 6.0 | 1143 |
| 250 | 2.66 | 0.35 | 9.1 | 2532 | 0.24 | 0.26 | 7.8 | 1637 |
| 500 | 3.44 | 0.46 | 11.7 | 2983 | 0.19 | 0.20 | 7.1 | 1841 |

[a]See Table II for explanation of abbreviations.

EXAMPLES 6-9

Table VI through IX provide data showing the inferior stabilization of dimethyl-2,6-naphthalenedicarboxylate provided by triphenyl phosphene (Example 6), pyrogallol (Example 7), TBHMPS (Example 8) and Pre-polymer (Example 9), respectively, compared to the stabilization provided by the organic phosphites used in Examples 2 through 5.

TABLE VI

Stabilization of DM-2,6-NDC with Triphenyl Phosphene[a]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 0 | 12.73 | 1 | 4.2 | 962 | 1.42 | 1 | 0 | 949 |
| 5 | 10.47 | 0.82 | 0 | 727 | 1.57 | 1.11 | 0 | 1205 |
| 12.5 | 12.4 | 0.97 | 0 | 754 | 2.49 | 1.75 | 0 | 965 |
| 25 | 12.53 | 0.98 | 0 | 961 | 1.44 | 1.01 | 0 | 878 |
| 50 | 14.23 | 1.12 | 0 | 776 | 3.41 | 2.40 | 7.1 | 1745 |
| 125 | 15.04 | 1.18 | 0 | 855 | 2.2 | 1.55 | 0 | 1170 |
| 250 | 16.62 | 1.31 | 5.5 | 1374 | 2.72 | 1.92 | 4.9 | 1615 |
| 500 | 21.27 | 1.67 | 6.6 | 1200 | 4.10 | 2.89 | 6.3 | 1633 |

[a]See Table II for explanation of abbreviations.

TABLE VII

Stabilization of DM-2,6-NDC with Pyrolgallol[a]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 0 | 8.59 | 1 | 6.4 | 822 | 0.91 | 1 | 0 | 1147 |
| 5 | 9.24 | 1.08 | 7.5 | 1005 | 1.08 | 1.19 | 5.5 | 1523 |
| 12.5 | 9.96 | 1.16 | 13.3 | 998 | 1.99 | 2.19 | 0 | 1343 |
| 25 | 10.66 | 1.24 | 10.2 | 976 | 4.09 | 4.49 | 0 | 651 |
| 50 | 8.47 | 0.99 | 9.9 | 595 | 1.18 | 1.30 | 0 | 496 |
| 125 | 8.6 | 1.00 | 10.6 | 392 | 1.26 | 1.38 | 0 | 285 |
| 250 | 5.86 | 0.68 | 0 | 470 | 1.26 | 1.38 | 0 | 399 |
| 500 | 4.98 | 0.58 | 4.7 | 483 | 1.02 | 1.12 | 0 | 272 |

[a]See Table II for explanation of abbreviations.

TABLE VIII

Stabilization of DM-2,6-NDC with TBHMPS[a, b]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 0 | 8.48 | 1 | 7.3 | 895 | 1.05 | 1 | 0 | 1063 |
| 5 | 10.04 | 1.18 | 6.8 | 1037 | 0.58 | 0.55 | 0 | 654 |

TABLE VIII-continued

Stabilization of DM-2,6-NDC with TBHMPS[a,b]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 10 | 3.45 | 0.41 | 5.5 | 471 | 3.32 | 3.16 | 0 | 918 |
| 25 | 4.87 | 0.57 | 6.8 | 550 | 2.16 | 2.06 | 0 | 368 |
| 50 | 5.43 | 0.64 | 5.8 | 779 | 0.83 | 0.79 | 6.4 | 454 |
| 125 | 7.28 | 0.86 | 14.8 | 1333 | 2.49 | 2.37 | 0 | 443 |
| 250 | 10.93 | 1.29 | 10.8 | 1648 | 1.97 | 1.88 | 8.8 | 375 |
| 500 | 13.37 | 1.58 | 13.6 | 1870 | 2.77 | 2.64 | 0 | 448 |

[a]3-t-Butyl-4-hydroxy-5-methylphenyl sulfide
[b]See Table II for an explanation of the other abbreviations.

TABLE IX

Stabilization of DM-2,6-NDC with Pre-Polymer[a,b]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 0 | 10.40 | 1 | 0 | 669 | 1.45 | 1 | 5.6 | 1595 |
| 50 | 10.46 | 1.01 | 0 | 780 | 0.85 | 0.59 | 0 | 1098 |
| 125 | 12.30 | 1.18 | 0 | 885 | 1.17 | 0.81 | 0 | 962 |
| 250 | 10.84 | 1.04 | 0 | 705 | 3.80 | 2.62 | 4.4 | 1313 |
| 500 | 12.02 | 1.16 | 5.8 | 1247 | 1.72 | 1.19 | 5.1 | 1392 |
| 1250 | 11.89 | 1.14 | 7.2 | 1340 | 4.22 | 2.91 | 9.3 | 1685 |
| 2500 | 9.37 | 0.90 | 5.6 | 1287 | 1.67 | 1.15 | 11.7 | 2402 |
| 5000 | 8.93 | 0.86 | 10.0 | 2854 | 1.11 | 0.77 | 12.5 | 3686 |

[a]See Table II for an explanation of abbreviations.
[b]Pre-polymer from Example 12

EXAMPLES 10-11

TABLE X

Stabilization of DM-2,6-NDC with Methanol[a]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 0 | 15.74 | 1 | 9.2 | 1881 | 0.85 | 1 | 9.7 | 2500 |
| 250 | 14.70 | 0.93 | 0 | 794 | 1.96 | 2.31 | 8.0 | 1948 |
| 500 | 10.38 | 0.66 | 0 | 611 | 4.53 | 5.33 | 5.9 | 1411 |
| 1000 | 10.73 | 0.68 | 0 | 846 | 1.67 | 1.96 | 7.4 | 1904 |
| 3000 | 3.94 | 0.25 | 4 | 1129 | 3.43 | 4.04 | 9.0 | 1597 |
| 5000 | 4.59 | 0.29 | 6.1 | 1525 | 0.32 | 0.38 | 11.0 | 2270 |
| 8000 | 1.29 | 0.08 | 17 | 3089 | 0.51 | 0.60 | 10.7 | 2321 |
| 10000 | 0.58 | 0.04 | 10.5 | 2273 | 6.83 | 8.04 | 16.5 | 2424 |

[a]See Table II for an explanation of abbreviations.

TABLE XI

Stabilization of DM-2,6-NDC with Ethylene Glycol[a]

| Stab. ppm | Air | | | | Nitrogen | | | |
|---|---|---|---|---|---|---|---|---|
| | CYIE | RYIE | ppm NDA | ppm MM NDC | CYIE | RYIE | ppm NDA | ppm MM NDC |
| 0 | 12.58 | 1 | — | 804 | 0.69 | 1 | 10.5 | 2521 |
| 1000 | 13.96 | 1.11 | 5.9 | 1271 | 2.47 | 3.58 | 13.5 | 2618 |
| 3000 | 13.60 | 1.08 | 5.8 | 1524 | 0.41 | 0.59 | 15.3 | 3782 |
| 5000 | 12.35 | 0.98 | — | 1409 | 0.75 | 1.09 | 15.5 | 5206 |
| 8000 | 13.91 | 1.11 | — | 1559 | 0.35 | 0.51 | 9.4 | 4295 |
| 10000 | 12.64 | 1.00 | 4.7 | 2523 | 0.30 | 0.43 | 10.8 | 6031 |
| 15000 | 7.29 | 0.58 | 7.0 | 5430 | | | | |

[a]See Table II for an explanation of abbreviations.

Table X presents data for methanol (Example 10), as a stabilizer for dimethyl-2,6-naphthalenedicarboxylate. At the 5,000 ppm level, methanol provides for excellent color stabilization of dimethyl-2,6-naphthalenedicarboxylate in both air and nitrogen atmospheres.

Table XI presents data showing that ethylene glycol (Example 11) is not an effective stabilizer for dimethyl-2,6-naphthalenedicarboxylate. Although ethylene glycol provides stabilization in samples tested in a nitrogen atmosphere, compared to methanol its performance is poor in samples tested using an air atmosphere.

EXAMPLE 12

A pre-polymer for the preparation of poly(ethylene-2,6-naphthalate) was prepared by charging to a 250 ml round bottom reaction flask 60 grams of dimethyl-2,6-naphthalenedicarboxylate and a transesterification catalyst containing calcium (41 ppm) and manganese (56 ppm). The flask and its contents were dried for 18 hours at 80° C. in a vacuum. The flask was then placed in an oil bath held at 200° C. While the mixture was melting, pre-heated anhydrous ethylene glycol was added. The amount of ethylene glycol added was an amount sufficient to provide 1.6 moles of ethylene glycol per mole of dimethyl-2,6-naphthalenedicarboxylate. Methanol was removed from the reaction flask through a 20 cm. Vigreux column. The reaction mixture was held at 200° C. for 120 minutes followed by gradual heating to 260° C. wherein a sweep of nitrogen was used to assist in the removal of volatile materials.

EXAMPLE 13

A prepolymer was prepared according to the procedure of Example 12 except that 10 moles of ethylene glycol were added per mole of dimethyl-2,6-naphthalenedicarboxylate, and only 50 grams of dimethyl-2,6-naphthalenedicarboxylate were reacted. Furthermore, the dimethyl-2,6-naphthalenedicarboxylate and 104 grams of ethylene glycol were heated first to form a melt. To this melt were added the catalyst metals dissolved in 22 grams of ethylene glycol.

The foregoing specification is illustrative of the disclosed invention and is not to be taken as limiting. Still other variations within the spirit and scope of the invention are possible and will be readily apparent to those skilled in the art.

I claim:

1. A stabilized composition consisting essentially of a substantially pure molten diester of a naphthalenedicarboxylic acid and a stabilizing effective amount of a stabilizer compound selected from the group consisting of low molecular weight monohydric alcohols and organic phosphites, wherein the stabilizing effective amount of the low molecular weight monohydric alcohol is about 1 to about 20,000 ppm by weight.

2. A stabilized composition consisting essentially of a diester of naphthalenedicarboxylic acid and a stabilizing effective amount of an organic phosphite stabilizer compound having structure

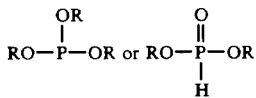

wherein R is a hydrocarbyl or substituted hydocarbyl group having 1 to 25 carbon atoms and wherein in each structure R may be the same or different.

3. The composition of claim 2 wherein said stabilizing effective amount of said stabilizer compound is about 0.01 to about 10,000 ppm by weight.

4. The composition of claim 2 wherein said diester of naphthalenedicarboxylic acid comprises dimethyl-2,6-naphthalenedicarboxylate.

5. The composition of claim 4 wherein said organic phosphite is selected from the group consisting of triphenyl phosphite, diphenyl phosphite, trimethyl phosphite and dimethyl phosphite.

6. The composition of claim 4 wherein said organic phosphite comprises triphenyl phosphite.

7. The composition of claim 2 wherein said diester of naphthalenedicarboxylic acid comprises dimethyl-2,6-naphthalenedicarboxylate prepared by the methanol esterification of 2,6-naphthalenedicarboxylic acid and wherein said 2,6-naphthalenedicarboxylic acid is prepared by the liquid-phase oxidation of 2,6-dimethylnaphthalene using a source of molecular oxygen and catalyzed by a catalyst comprising cobalt, manganese and bromine components.

8. The composition of claim 2 wherein said diester of naphthalenedicarboxylic acid is substantially pure.

9. A stabilized composition comprising a substantially pure diester of a naphthalenedicarboxylic acid in the molten state and about 1 to about 20,000 ppm by weight of a low molecular weight monohydric alcohol having 1 to 4 carbon atoms.

10. The composition of claim 9 wherein said low molecular weight monohydric alcohol is methanol.

11. The composition of claim 10 wherein said diester of naphthalenedicarboxylic acid comprises dimethyl-2,6-naphthalenedicarboxylate.

12. The composition of claim 11 wherein said dimethyl-2,6-naphthalenedicarboxylate has been purified by distillation, crystallization, or a combination thereof, and is at least about 99% pure.

13. The composition of claim 9 wherein said low molecular weight monohydric alcohol is present in said composition in an amount of about 50 to about 10,000 ppm by weight.

14. The composition of claim 11 wherein said dimethyl-2,6-naphthalenedicarboxylate is prepared by the methanol esterification of 2,6-naphthalenedicarboxylic acid and wherein said 2,6-naphthalenedicarboxylic acid is prepared by the liquid-phase oxidation of 2,6-dimethylnaphthalene using a source of molecular oxygen and catalyzed by a catalyst comprising cobalt, manganese and bromine components.

15. The composition of claim 2 wherein said composition is molten.

16. The composition of claim 2 wherein said composition is solid and said stabilizing effective amount of said stabilizer compound is the amount required to stabilize said composition when said composition is molten.

17. A method for stabilizing a diester of a naphthalenedicarboxylic acid while maintained in the molten form comprising treating said diester of a naphthalenedicarboxylic acid with a stabilizing effective amount of a stabilizer compound selected from the group consisting of low molecular weight monohydric alcohols and organic phosphites wherein the amount of low molecular weight alcohol in the molten diester is about 1 to about 20,000 ppm by weight.

18. The method of claim 17 wherein said treating comprises adding said stabilizer compound to said diester of naphthalenedicarboxylic acid while said diester of naphthalenedicarboxylic acid is a solid.

19. The method of claim 17 wherein said treating comprises adding said stabilizer compound to said diester of naphthalenedicarboxylic acid while said diester of naphthalenedicarboxylic acid is molten.

20. The method of claim 17 wherein said stabilizer compound is an organic phosphite having a structure

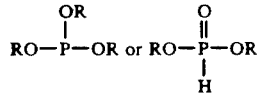

wherein R is a hydrocarbyl or substituted hydrocarbyl group having 1 to 25 carbon atoms and wherein in each structure R may be the same or different.

21. The method of claim 20 wherein said stabilizing effective amount of said stabilizer compound is about 0.01 to about 10,000 ppm by weight.

22. The method of claim 20 wherein said diester of naphthalenedicarboxylic acid comprises dimethyl-2,6-naphthalenedicarboxylate.

23. The method of claim 22 wherein said organic phosphite is selected from the group consisting of triphenyl phosphite, diphenyl phosphite, trimethyl phosphite and dimethyl phosphite.

24. The method of claim 22 wherein said organic phosphite is triphenyl phosphite.

25. The method of claim 17 wherein said stabilizer compound is a low molecular weight monohydric alcohol having 1 to 4 carbon atoms.

26. The method of claim 25 wherein said low molecular weight alcohol is methanol.

27. The method of claim 26 wherein said diester of a naphthalenedicarboxylic acid comprises dimethyl-2,6-naphthalenedicarboxylate.

28. The method of claim 17 wherein said diester of naphthalenedicarboxylic acid is at least about 99% pure.

29. The method of claim 25 wherein said stabilizing effective amount of said low molecular weight monohydric alcohol is about 50 to about 10,000 ppm by weight.

* * * * *

UNITED STATES PATENT OFFICE
CERTIFICATE OF CORRECTION

Patent No.   5,138,025                    Dated   AUGUST 11, 1992

Inventor(s)   ALLEN B. MOSSMAN

It is certified that error appears in the above-identified patent and that said Letters Patent is hereby corrected as shown below:

<u>Column</u>   <u>Line</u>

14   Table II          "<u>Nitrogen</u><sup>c</sup>

<u>Stab.</u>
          <u>ppm</u>          <u>RYIE</u>

125           01.6 "   should read:

-- <u>Nitrogen</u><sup>c</sup>

<u>Stab.</u>
          <u>ppm</u>          <u>RYIE</u>

125           0.16 --

Signed and Sealed this

Twelfth Day of October, 1993

*Attest:*

BRUCE LEHMAN

*Attesting Officer*     Commissioner of Patents and Trademarks